US006686192B1

(12) United States Patent
Sturino et al.

(10) Patent No.: US 6,686,192 B1
(45) Date of Patent: Feb. 3, 2004

(54) ANTISENSE RNA EXPRESSION STRATEGIES EFFECTIVE AGAINST STREPTOCOCCUS THERMOPHILUS BACTERIOPHAGES

(75) Inventors: Joseph Miland Sturino, Raleigh, NC (US); Todd Robert Klaenhammer, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 45 days.

(21) Appl. No.: 09/642,894

(22) Filed: Aug. 21, 2000

(51) Int. Cl.$^7$ .......................... C07H 21/04; C12Q 1/68; C12N 1/20
(52) U.S. Cl. ..................... 435/253.4; 435/6; 435/320.1; 536/23.1; 536/24.1; 536/24.5
(58) Field of Search ...................... 435/6, 320.1, 253.4; 536/23.1, 24.1, 24.5

(56) References Cited

U.S. PATENT DOCUMENTS 5,538,864 A    7/1996   Hill et al.

OTHER PUBLICATIONS

Sturino, Joseph M., et al., *Expressioni of Antisense RNA Targeted against Streptococcus thermophilus Bacteriophages, Applied and Environmental Microbiology*, vol. 68, No. 2, pp. 588–596 (Feb. 2002).
Excerpt, Ph.D. Thesis of Shirley Walker, pp. 50–51 (1999).
Sturino, Joseph M., et al., *Construction of Effective Antisense Phage Defense Strategies for Lactic Acid Bacteria, Molecular Genetics of Bacteria & Phages* (2000).
Sturino, Joseph M., et al., *Targeting Phage DNA Replication Functions with Antisense RNA, Molecular Genetics of Bacteria & Phages* (2000).
Walker, Shirley A., et al, *Molecular Characterization of a Phage–Inducible Middle Promoter and Its Transcriptional Activator from the Lactococcal Bacteriophage φ31, Journal of Bacteriology*, vol. 180, No. 4, pp. 921–931 (Feb. 1998).
International Search Report, International Application No. PCT/US01/26033 dated Feb. 21, 2002.
Tremblay, et al., *Complete Genomic Sequence of the Lytic Bacteriophage DTI of Streptococcus thermophilus, Virology*, vol. 255, pp. 63–76 (1999).
Brüssow, Harald, et al., *Molecular Ecology and Evolution of Streptococcus thermophilus Bacteriophages—a Review, Virus Genes*, vol. 16, No. 1, pp. 95–109 (1998).

Bruttin, Anne, et al., *Molecular Ecology of Streptococcus thermophilus Bacteriophage Infections in a Cheese Factory, Applied and Environmental Microbiology*, vol. 63, No. 8, pp. 3144–3150 (1997).
Foley, Sophie, et al., *A Short Noncoding Viral DNA Element Showing Characteristics of a Replication Origin Confers Bacteriophage Resistance to Streptococcus thermophilus, Virology*, vol. 250, pp. 1–11 (1998).
Stanley, Elizabeth, et al., *Identification of four loci isolated from two Streptococcus thermophilus phage genomes responsible for mediating bacteriophage resistance, FEMS Microbiology Letters*, vol. 182, pp. 271–277 (2000).
Wigley, R.C., et al., *Starter Cultures: Uses in the Food Industry*, pp. 2084–2108 (1999).
Schleifer, Karl Heinz, et al., *Revival of the Species Streptococcus thermophilus (ex Orla–Jensen, 1999) nom. rev., System Appl. Microbiol.*, vol. 14, pp. 386–388 (1991).
Le Marrec, Claire, et al., *Two Groups of Bacteriophages Infecting Streptococcus thermophilus Can Be Distinguished on the Basis of Mode of Packaging and Genetic Determinants for Major Structural Proteins, Applied and Environmental Microbiology*, vol. 63, No. 8, pp. 3246–3253 (Aug. 1997).
Bull, J.J., et al., *Viral escape from antisense RNA, Molecular Microbiology*, vol. 28, No. 4, pp. 835–846 (1998).
Coleman, Jack, et al., *A novel immune system against bacteriophage infection using complementary RNA (micRNA), Nature*, vol. 315, pp. 601–603 (Jun. 1985).
Hill, C., et al., *Future Prospects for Culture Improvement, Dairy Starter Cultures*, pp. 249–255.
Walker, Shirley A., et al., *An Explosive Antisense RNA Strategy for Inhibition of a Lactococcal Bacteriophage, Applicated and Environmental Microbiology*, vol. 66, No. 1, pp. 310–319 (Jan. 2000).
Zirnstein, Gerald, et al., *Streptococcus thermophilus, Streptococcus*, pp. 2127–2133.

*Primary Examiner*—Sean McGarry
(74) *Attorney, Agent, or Firm*—Myers Bigel Sibley & Sajovec

(57) ABSTRACT

Recombinant bacteria containing nucleotide sequences encoding *Streptococcus thermophilus* phage helicase and primase genes expressed in the antisense orientation and methods of making and using the same are disclosed. Replication of bacteriophage infecting this bacterial cell, can be inhibited or decreased by constitutively expressing, the antisense oligonucleotide encoding for *S. thermophilus* phage helicase or primase.

20 Claims, 5 Drawing Sheets

SEQUENCE LISTING

<160> NUMBER OF SEQ ID NOS: 9

<210> SEQ ID NO 1
<211> LENGTH: 1332
<212> TYPE: DNA
<213> ORGANISM: Streptococcus thermophilus bacteriophage

<400> SEQUENCE: 1

| | | | | | |
|---|---|---|---|---|---|
| atggaactaa | ggaattacca | gaatgatctt | gttaatggga | tcaagcaatc | aatcttaaga | 60 |
| ggtaacaagc | gaattatggt | gcagtcgcca | ccacgtagtg | gcaaaaccgt | tgtaatggct | 120 |
| catattgcca | aaggtgcaac | agataaaggt | aaxaxtgttc | tattctttag | ccatcgaaag | 180 |
| gaaattaatg | agcaggtagt | caatacattc | aaaagaaatg | gcgttgacat | gaaccttgta | 240 |
| accattgata | gcgtgactaa | ggtagcacga | aacctagata | ggatatcaga | gccatcgatc | 300 |
| atattaatcg | acgaagctca | ccatgttaaa | gctaagacct | acctcaaaat | tatcgaatat | 360 |
| tacattaaca | gcattgttct | catgtttact | gggacacccg | ccagactaga | tggcagtggg | 420 |
| tttgatgata | tcgcagacga | cattgttctc | ggaaagtcgg | ttaaatggct | acaggagaac | 480 |
| gggaacatcg | caccatttaa | atattatgcc | ccttctttaa | tcgacactac | aaacctaaaa | 540 |
| aagcgtggtg | gagagtttac | taagaaatcc | gtagacgaca | caatgaaacg | tgtgatttac | 600 |
| ggtgatgtta | taagacatta | tgagaagtta | gccaaaggca | aacaagccat | agtatacaca | 660 |
| catagcgtag | aagcttctga | gagcgtttct | aacacgttta | aaaagaatgg | ctatacttct | 720 |
| atcgcaatca | gtggtaaaac | gccaccagag | gttcgagaga | gggcaatgca | aacctttaga | 780 |
| gacagagaac | ttacaattat | ggttaattgt | gagttattca | ctgaaggtat | tgaccttcca | 840 |
| aatgttgatg | tttgcatcat | gctaagacca | actcaatcat | tatctttata | tcttcagttt | 900 |
| gctatgagag | ccttaaaccc | tagagaagga | aaaacagcta | tcataataga | ccacgttggc | 960 |
| aatgttgata | gacatggact | tccaaacgct | gaccgtgaat | ggtcactaaa | gggtattaat | 1020 |
| aaaactaaaa | aaaaacttaa | actcggtgaa | cctaccacac | ggacgtgtga | tgaatgctac | 1080 |
| gctacgtttt | ggagtgctga | acgtatctgt | ccactgtgtg | gccatgagaa | tcagcctaca | 1140 |
| aaagaagaaa | ttgaaataat | tcgagaaata | gaactcgaag | aaagacggca | agaggttgct | 1200 |
| agtaaagttg | aaacattcgt | tactagtgac | caatgccaat | cagtagaaga | actcaaagag | 1260 |
| ttcgctaaac | aacacggata | taaacccggt | tgggtttatt | accaacagaa | aaaaaataat | 1320 |
| atatggagat | aa | | | | | 1332 |

<210> SEQ ID NO 2
<211> LENGTH: 1501
<212> TYPE: DNA
<213> ORGANISM: Streptococcus thermophilus bacteriophage

<400> SEQUENCE: 2

| | | | | | |
|---|---|---|---|---|---|
| ttgacaacga | ttgatttcga | ttattacaga | gaacaatttg | caagctctac | tctctcacca | 60 |

-continued

```
agtaaaccga gcagcagaga gggaattaag aataagctta aagcctaccg aaacgactgg       120
tttgaaaaat tcaaggaaga aaatccagat agcaaagaac caaaggcatt gccagaatta       180
gcagtagcta aaggtttaaa taaatacact catgttatca ccctcgaaaa tgggaaagta       240
gctatatatg atccagagcg gggatactac caaaaagatt acagatatgc ctaccagctt       300
atctatatct tagaacctac attcaatgaa acaaaatgcc gaaatgttct attttttgcta      360 tcaaacatga gcagggaata tgaatataat aacatgtata tggattttga accagaatat      420
cgagatgtaa ggcgttttat tctcgttaaa atggcatct acgataaacg aaagaagaag        480
ctgctatcgt ttgaccataa gtttattaat tttagtacca ttgaaacaga actggtcgag       540 aatgcccta aaccaattat taatggttgg gatgtcgata gttggttgtt agatctcatg        600
agtggcgaca gtgagcttgt agaattacta tggcaagtga ttgcagcgtc acttaatggt       660
aaccattctt atcgaaaatc gatgtggtta gttggtaacg gtaacgatgg taagggtacg       720
tttcaacagt tgattagcaa tttggttgga ttaaaaaacg tagcaccatt aaaaattaat      780
caattttctg aacgtttcgg tcttgccatt attgaaggga agacagttat cattggtgac     840
gatgtccaag ctggtatata tgtagatgaa tcttccaatt ttaactcagt cgttactggt       900
gaaccagttt caattgagaa aaaaggagaa atccttact tagcgcaatt taagaaaacg        960
gttatccagt ctaccaatgc tatgccagtg tttaagaata agtcaaacgg tacatatcga     1020
cgtatcgtga ttatcccatt caaaaaaaca tttggcatca atgatgacaa ttgggcaatt      1080
aaggatgatt acatcaatcg taaagaagtt ttggaatatg ttctttggaa agcaattaat     1140
ttagattttg acaaattcaa cgaaccaaaa gcgacacaag aacgtatgca agagttcaag     1200
gaagaaaata acacagttta taattccctt aatgaatact tgtcagatgt cgtttccact    1260
cgaattccag ttaggttctt gtgggatgta taccgctcat ggtgtcatga gggaaatcat     1320
actataccta aaaaatctaa cttttgaaaaa gagctggcac agaatttacc ggtaggttgg    1380
attaaagata gacaaaaacc tcttgatttt tttaatccaa ctaaagataa gccagattat    1440
tggcatgatt tcaatttaa ttgggacgaa acgaggcga agaaagcagc agtagtggtt      1500
a                                                                   1501
```

<210> SEQ ID NO 3
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 3

```
aaactgcagg cttgcaagat tgaagacc                                         28
```

<210> SEQ ID NO 4
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 4

```
aaactgcagc cgtctttgat agatccg                                          27
```

<210> SEQ ID NO 5
<211> LENGTH: 18
<212> TYPE: DNA
<213> ORGANISM: Artificial Sequence

```
<220> FEATURE:
<223> OTHER INFORMATION: Synthetic oligonucleotide

<400> SEQUENCE: 5
ggagcgtgat ttttatgg                                              18

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 6
gttaaagcta agacctacc                                             19

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
ccctttagtg accattcacg g                                          21

<210> SEQ ID NO 8
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 8
ggaattccac ttgtcagatg tcgtttcc                                   28

<210> SEQ ID NO 9
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 9
ggaattcccc ataatcttcg tcggtcc                                    27
```

US 6,686,192 B1

ANTISENSE RNA EXPRESSION STRATEGIES EFFECTIVE AGAINST *STREPTOCOCCUS THERMOPHILUS* BACTERIOPHAGES

STATEMENT OF FEDERAL SUPPORT

This invention was made with government support under grant number 97-35503-4368 from the United States Department of Agriculture National Research Initiative. The United States government has certain rights to this invention.

FIELD OF THE INVENTION

The present invention relates to bacteriophage resistant recombinant bacteria and their use in fermentation.

BACKGROUND OF THE INVENTION

The dairy industry has harnessed certain members of the heterogeneous group of lactic acid bacteria, including the thermophilic bacterium *Streptococcus thermophilus*, as starter cultures or culture adjuncts to drive the lactate fermentations in the manufacture of a variety of fermented products. This organism grows best at the high end of the mesophilic range, about 42–25° C., thus it survives and produces acid at temperatures higher than can be tolerated by the mesophilic lactic acid bacteria. This characteristic makes *S. thermophilus* useful in the fermentation of dairy products, such as yogurt and Swiss and Italian cheeses, that are ordinarily manufactured or incubated at elevated temperatures.

Pasteurized milk, the primary substrate for fermented products, and in some instances the starter cultures themselves, have been be shown to be a natural reservoir for virulent bacteriophages capable of infecting and, inevitably, lysing the starter culture(s) during product manufacture (Bruttin et al, *Appl. Environ. Microbiol.* 63:3144–3150 (1997); Moineau et al., *J Dairy Sci.* 79:2104–2111 (1996)). Depending upon the severity and temporal progression of the lytic infection, the concomitant loss of fermentative capacity associated with starter culture lysis can significantly retard or halt batch fermentations; thereby inflicting upon the dairy industry significant losses of time and production capital each year. With the advent of biotechnology, the dairy industry is seeking to identify novel phage defense strategies capable of extending the utility of industrial starter cultures.

Expression of antisense RNA silences gene expression in vivo through the formation of a double stranded target mRNA::antisense RNA duplexes (Inouye, M. *Gene* 72:25–34 (1988)). Duplex formation is believed to interfere with protein translation by (i) masking the ribosome binding site (RBS), which prevents ribosome loading, and/or (ii) destabilizing the mRNA by targeting it for RNase-mediated degradation (Inouye, M. *Gene* 72:25–34 (1988)). In theory, the best candidates for effective silencing by means of antisense RNA strategies will be genes that are (i) essential for bacteriophage maturation, (ii) transiently expressed and/or coded for by unstable mRNA species, (iii) expressed at low levels and/or expressed early, (iv) inefficiently translated, and (v) coded for by mRNA species that form secondary structures that are conducive to recognition of the antisense RNA molecule.

SUMMARY OF THE INVENTION

A first aspect of the present invention is an antisense oligonucleotide and a nucleic acid encoding an antisense oligonucleotide that binds to a bacterial cell bacteriophage RNA and inhibits the replication of that bacteriophage in a host bacterial cell (e.g., *Streptococcus thermophilius*). For example, the RNA targeted by the antisense oligonucleotide may be mRNA encoding a bacteriophage protein, such as a phage helicase or a phage primase. The present invention may be carried out with any bacteriophage, including cos-type and pac-type bacteriophage. The antisense oligonucleotide is preferably at least 8 nucleotides in length. Examples include antisense oligonucleotides that comprise a continuous fragment at least 8 nucleotides in length, in antisense orientation, of the sequences given herein as SEQ ID NO: 1 or SEQ ID NO: 2.

A second aspect of the present invention is a construct comprising a promoter that is operably associated with the oligonucleotide described above. The promoter regulates transcription of the oligonucleotide in the antisense orientation, such that a sufficient amount of antisense RNA is transcribed to block translation of the phage-encoded replication machinery. Preferably the promoter regulates transcription of the antisense RNA constitutively.

A third aspect of the present invention comprises a bacterial cell, preferably *S. thermophilus*, which harbors a recombinant DNA vector containing an oligonucleotide as which encodes an antisense oligonucleotide as described above.

A fourth aspect of the present invention involves a recombinant nucleic acid vector comprising a bacteriophage origin of replication (ori) operatively associated with a nucleic acid sequence that blocks translation of phage-encoded replication machinery. When a bacterial cell, harboring the nucleic acid vector, is infected with phage, the nucleic acid vector exponentially replicates to increase the dose of antisense RNA.

These aspects are more completely described hereinbelow. In addition, other aspects of the present invention not explicitly set forth herein will become apparent to those skilled in the art.

DETAILED DESCRIPTION OF PREFERRED EMBODIMENTS

Figure 1:
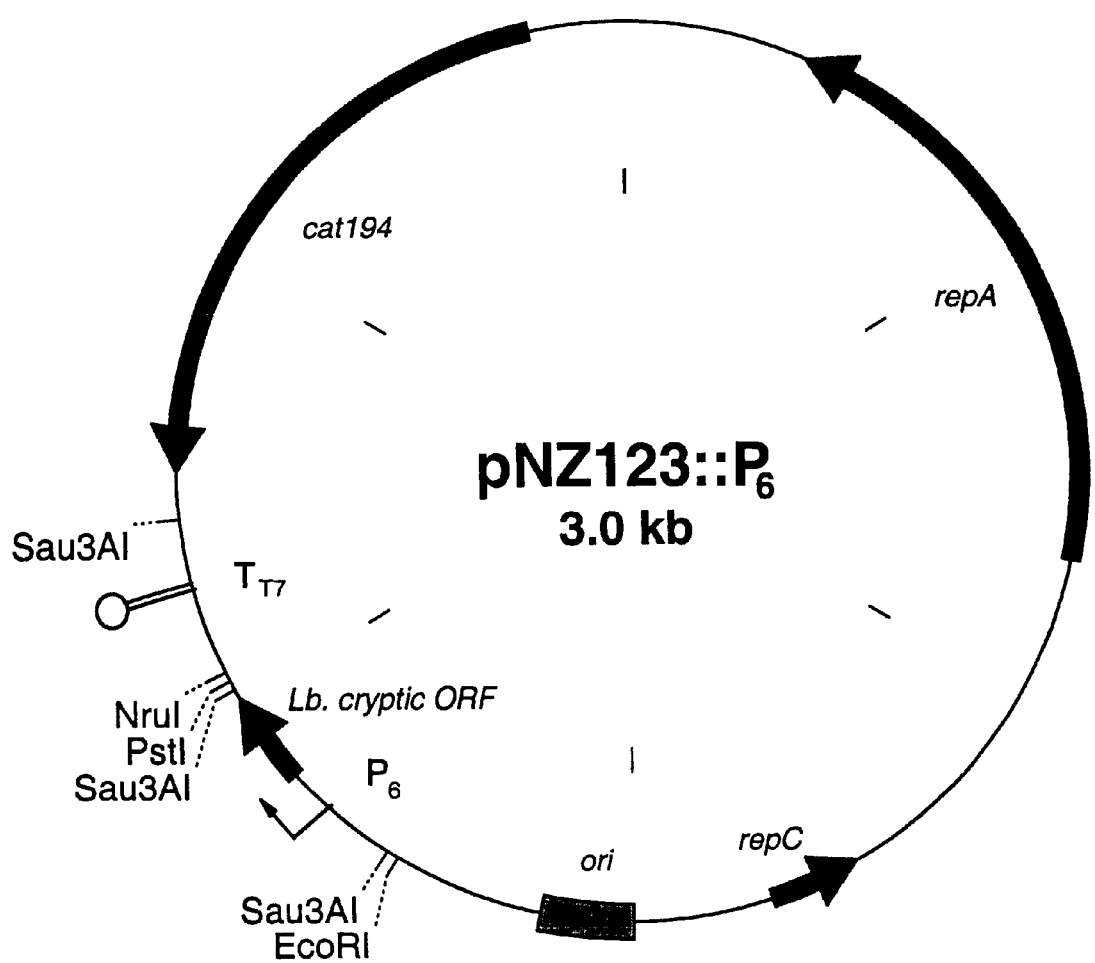
FIG. 1 depicts high-copy number basal RNA expression vector pNZ123::$P_6$. The BglII fragment containing the $P_6$ promoter and coliphage T7 transcriptional terminator isolated from pTRK593 was cloned into the Sau3AI site of pNZ123.

Except as otherwise indicated, standard methods may be used for the production of cloned genes, vectors, and transformed cells according to the present invention. Such techniques are known to those skilled in the art (see e.g., SAMBROOK et al., EDS., MOLECULAR CLONING: A LABORATORY MANUAL 2d ed. (Cold Spring Harbor, N.Y. 1989); F. M. AUSUBEL et al, EDS., CURRENT PROTOCOLS IN MOLECULAR BIOLOGY (Green Publishing Associates, Inc. and John Wiley & Sons, Inc., New York).

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

The present invention describes the use of antisense suppression to target the bacteriophage-encoded helicase (hel) and primase (pri) genes because they (i) may be essential for efficient replication of bacteriophage DNA, (ii) may be expressed early in the lytic life cycle in other systems and, (iii) are highly conserved at the nucleotide level by all sequenced *S. thermophilus* bacteriophages currently in the database.

The present investigations demonstrate that replication of bacteriophage, which infect *S. thermophilus,* can be inhibited by constitutively expressing, in the antisense orientation, an oligonucleotide encoding for *S. thermophilus* phage helicase or primase. A recombinant DNA vector containing said oligonucleotide can be a high-copy number plasmid or contain a phage origin of replication, that upon infection by phage, replicates exponentially.

In general, the antisense oligonucleotide is one which binds to phage RNA and inhibits the replication of the phage in its corresponding host cell. For example, the antisense oligonucleotide could be one which inhibits the production of a phage protein, such as phage helicase or phage primase. Inhibition of such a protein could be carried out with an antisense oligonucleotide that binds to mRNA encoding that protein, or to other RNA of the polycistronic message that contains the mRNA encoding the protein targeted for downregulation.

By "isolated" when referring to a nucleotide sequence, is meant that the indicated molecule is present in the substantial absence of other biological macromolecules of the same type. Thus, an "isolated nucleic acid" refers to a nucleic acid molecule which is substantially free of other nucleic acid molecules; however, the molecule may include some additional bases or moieties which do not deleteriously affect the basic characteristics of the composition.

The term "oligonucleotide" refers to a nucleic acid sequence of at least about 8 nucleotides to about 1700 nucleotides, preferably about 1000 to 1500 nucleotides.

Exemplary *S. thermophilus* phage include, but are not limited to those of the cos-type and pac-type, preferably of the cos-type. Members of the cos-type include, but are not limited to DT1, Φ83, Φ117, PO, Φ71, Φ124, Φ47, st2, BaS19, Q5, Φ7201, Φ7203, Φ7205, Φ7206, Φ7209, Φ8FN, Φ33, c20, BaS265, and Q6. Member of the pac-type include, but are not limited to P4, Φ31, Φ11, Φ1, Φ4FN, Φ45, O1205, 447-B4, Q1, Q3, Q7, and Q10.

"Antisense orientation" refers to a nucleic acids transcribed in the 5'-to-3' direction. The resulting RNA transcript is complementary to all or part of a target primary transcript or mRNA blocking the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, or the coding sequence.

By "recombinant nucleic acid" is meant a vector molecule that has been genetically altered, e.g., by the addition or insertion of a heterologous nucleic acid construct into the cloning vector. A "cloning vector" is a DNA molecule, such as a plasmid, cosmid, or integratable DNA fragments (i.e., fragments integratable into the host genome by recombination).

Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance, chloramphenicol resistance, or ampicillin resistance.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

While the present invention is, in a preferred embodiment, directed to the fermentation of food, the invention may be practiced with any fermentation process susceptible to disruption by bacteriophage infection, including processes for the production of antibiotics, amino acids, and solvents. Products produced by fermentation which are known to have encountered bacteriophage infection, and the corresponding infected fermentation bacteria, include Cheddar and cottage cheese (*Lactococcus lactis, Lactococcus cremoris*), Yogurt (*Lactobacillus bulgaricus, S. thermophilus*), Swiss cheese (*S. thermophilus, Lactobacillus lactis, Lactobacillus helveticus*), Blue cheese (*Leuconostoc cremoris*), Italian cheese (*L. bulgaricus, S. thermophilus*), Viili (*Lactococcus cremoris, Lactococcus lactis* subsp. *diacetylactis, Leuconostoc cremoris*), Yakult (*Lactobacillus casei*), casein (*Lactococcus cremoris*), Natto (*Bacillus subtilis* var. natto), Wine (*Leuconostoc oenos*), Sake (*Leuconostoc mesenteroides*), Polymyxin (*Bacillus polymyxa*), Colistin (*Bacillus colistrium*), Bacitracin (*Bacillus licheniformis*), L-Glutamic acid (*Brevibacterium lactofermentum, Microbacterium ammoniaphilum*), and acetone and butanol (*Colstridium acetobutylicum, Clostridium saccharoperbutylacetonicum*). See generally M. Sanders, Bacteriophages of Industrial Importance, in PHAGE ECOLOGY, 211–44 (S. Goyal, C. Berba and G. Bitton eds. 1987). Thus, the present invention may, for example, be employed in a fermentation process for producing any of the foregoing products with the foregoing bacteria in the manner described herein.

Bacteria capable of fermenting foods include those bacteria used in any type of food fermentation, including, but not limited to, the fermentation of milk, egg, meat, fruit, vegetables, and cereals. See generally Food Biotechnology, (D. Knorr Ed. 1987)(Marcel Dekker, Inc.); Fermented Foods (A. Rose Ed. 1982)(Academic Press); C. Pederson, Microbiology of Fermented Foods, (2d ed. 1979)(AVI Publishing Co.).

Milk is fermented to produce products such as cheese, yogurt, kefir, and acidophilus milk. Cheese fermentation bacteria are discussed separately below. Otherwise, bacteria used for the fermentation of milk include, but are not limited to, Lactobacillus bulgaricus, Lactobacillus acidophilus, S. thermophilus, and mixtures thereof. See Food Biotechnology, 530 (D. Knorr Ed. 1987); C. Pederson, Microbiology of Fermented Foods, 105–35 (2d ed. 1979).

Bacteria used for the fermentation of milk to produce cheese include, but are not limited to, Lactobacillus bulgaricus, Lactobacillus helveticus, S. thermophilus, Lactococcus lactis, Lactococcus cremoris, Lactococcus lactis subsp. diacetylactis, and mixtures thereof. See Food Biotechnology, 530 (D. Knorr Ed. 1987); C. Pederson, Microbiology of Fermented Foods, 135–51 (2d ed. 1979).

Bacteria used for the fermentation of egg include Pediococcus cerevisiae, Lactobacillus plantarum, and mixtures thereof. See Food Biotechnology, 538–39 (D. Knorr Ed. 1987).

Bacteria used for the fermentation of meat (including beef, pork, and poultry) include, but are not limited to, lactic acid bacteria, Pediococcus cerevisiae, Lactobacillus plantarum, Lactobacillus brevis, Micrococcus species, Leuconostoc citrovorum, and mixtures thereof. See Food Biotechnology, 538–39 (D. Knorr Ed. 1987); C. Pederson, Microbiology of Fermented Foods, 210–34 (2d ed. 1979); U.S. Pat. No. 2,225,783 to Jensen and Paddock.

Bacteria used for the fermentation of vegetables (e.g., carrots cucumbers, tomatoes, peppers, and cabbage) include, but are not limited to, Lactobacillus plantatum, Lactobacillus brevis, Leuconostoc mesenteroides, Pediococcus cerevisiae, and mixtures thereof. See Food Biotechnology, 540 (D. Knorr Ed. 1987); C. Pederson, Microbiology of Fermented Foods, 153–209 (2d ed. 1979); U.S. Pat. No. 3,024,116 to Engelland; U.S. Pat. No. 3,403,032 to Etchells et al.; U.S. Pat. No. 3,932,674 to Etchells et al.; U.S. Pat. No. 3,897,307 to Porubcan et al.

Organisms used in the fermentation of dough formed from cereals (e.g., wheat, rye, rice, oats, barley, and corn) include yeasts such as Saccharomyces cerevisiae and Candida utilis; and lactic acid bacteria of the genera Lactobacillus, Lactococcus, Pediococcus and Leuconostoc, including, but not limited to Lactobacillus delbrueckii, Lactobacillus leichmanni, Lactobacillus plantarum, Lactobacillus casei, Lactobacillus brevis, Lactobacillus fermenti, Lactobacillus pastorianus, Lactobacillus buchneri, and Leuconostoc mesenteroides. See generally Food Biotechnology, 235–70 (D. Knorr Ed. 1987); U.S. Pat. No. 3,734,743 to Kline and Sugihara; U.S. Pat. No. 3,681,083 to Everson; U.S. Pat. No. 3,993,783 to Khoudokormoff and Langejan; U.S. Pat. No. 3,843,800 to Langejan; U.S. Pat. No. 3,410,692 to Wutzel.

Wine is produced by the fermentation of fruit juice, typically grape juice, with yeasts, such as Saccharomyces cerevisiae and Saccharomyces ellipsoideus, as well as with a broad variety of lactic acid bacteria including Pediococcus cerevisiae, Lactobacillus plantarum, Leuconostoc mesenteroides, Leuconostoc dextranicum, Leuconostoc cremoris, Lactobacillus brevis, and Lactobacillus fermenti.

Beer is produced by the fermentation of malt with yeasts such as Saccharomyces cerevisiae and Saccharomyces carlsbergensis. See C. Pederson, Microbiology of Fermented Foods, 271–309 (2d ed. 1979).

In a particularly preferred embodiment, the present invention is employed for the fermentation of milk with Streptococcus thermophilus.

Starter cultures employed in practicing the present invention may be in any physical form, including liquid cultures of the fermentation bacteria in a suitable growth medium, as well as lyophilized cultures, immobilized cells, and frozen cultures prepared therefrom.

Starter cultures employed in the present invention are preferably defined cultures (i.e., cultures of known bacterial content). Such defined cultures may be either single strain cultures or multiple strain cultures.

The examples, which follow, are set forth to illustrate the present invention, and are not to be construed as limiting thereof. In the following examples, w/v means weight per volume, v/v means volume per volume, $\mu$g means microgram, ml means milliliter, Cm means chloramphenicol, $\mu$F means micro Faraday, kV means kilovolts, $\Omega$ means Ohms, kb means kilo base pair, and temperatures are given in degrees Celsius (° C.).

EXAMPLE 1

Materials and Methods

Bacterial Strains and Media. The bacterial strains used are listed in Table 1. All cultures were maintained at −80° C. in Elliker broth supplemented with 1% (w/v) beef extract (Elliker-B) and 10% (v/v) glycerol. All bacteriological media and components were purchased from Difco Laboratories (Detroit, Mich.). Unless otherwise indicated, E. coli MC1061 (Calander, 1980. J. Mol. Biol. 138:179–210) and derivatives were grown at 37° C. with constant aeration in Luria-Bertani broth (Maniatis et al.. 1982. Molecular cloning: a laboratory manual, Cold Spring Harbor Laboratory, Cold Spring Harbor. N.Y.) and S. thermophilus MTC130 and derivatives were grown at 42° C. in Elliker-B broth. When appropriate, chloramphenicol (Cm) was added at the following concentrations: for E. coli, Cm at 5 $\mu$g/ml; for S. thermophilus, Cm at 3 $\mu$g/ml. For solid media, Bacto Agar was added at a final concentration of 1.5% (w/v) for base agar and 0.8% (w/v) for soft agar.

TABLE 1

| Bacterial strain or bacteriophage | Relevant characteristics |
|---|---|
| Streptococcus thermophilus | |
| MTC130 | Parental strain; $\kappa 3^S$, $\kappa 6^S$; $Cm^S$ |
| MTC130 (pNZ123) | $\kappa 3^S$, $\kappa 6^S$; $Cm^R$ |
| MTC130 (pNZ123::P$_6$) | $\kappa 3^S$, $\kappa 6^S$; $Cm^R$ |
| MTC130 (pNZ123::P$_6$::he13-S) | $\kappa 3^S$, $\kappa 6^S$; $Cm^R$ |
| MTC130 (pNZ123::P$_6$::he13-AS) | $\kappa 3^R$, $\kappa 6^S$; $Cm^R$ |
| MTC130 (pNZ123::P$_6$::pri3$\Delta$RBS-S) | $\kappa 3^S$, $\kappa 6^S$; $Cm^R$ |

TABLE 1-continued

| Bacterial strain or bacteriophage | Relevant characteristics |
|---|---|
| MTC130 (pNZ123::P$_6$::pri3Δ RBS-AS) | κ3$^R$, κ6$^S$; Cm$^R$ |
| *Escherichia coli* | |
| MC1061 (Calander, J Mol. Biol. 138: 179–210 (1980)). | ara leu lacX74 galU galK hsdB hsdM strA |
| Bacteriophages | |
| κ3 | cos-type bacteriophage isolated from whey |
| κ4 | cos-type bacteriophage isolated from whey |
| κ6 | pac-type bacteriophage isolated from whey |
| κ9 | cos-type bacteriophage isolated from whey |
| κ10 | cos-type bacteriophage isolated from whey |
| κ12 | pac-type bacteriophage isolated from whey |

Abbreviations: Cm$^R$, chloramphenicol resistance; Cm$^S$, chloramphenicol sensitive; κ3$^S$, sensitive to phage κ3; κ3$^R$, resistant to phage κ3; κ6$^S$, sensitive to phage κ6.

Enzymes and Chemicals. Restriction enzymes, Taq polymerase, and deoxynucleoside triphosphates were obtained from Boehringer Mannheim (Indianapolis, Ind.). T4 DNA ligase and DNA molecular weight markers were obtained from Gibco BRL Life Technologies (Gaithersburg, Md.). All other chemicals were of analytical grade and obtained from Sigma Chemical Company (St. Louis, Mo.).

DNA Purification. Plasmid DNA was isolated from *E. coli* according to standard methods (Maniatis, T., E. F. Fritsch, and J. Sambrook. (1982) *Molecular Cloning: a laboratory manual,* Cold Spring Harbor Laboratory, Cold Spring Harbor. N.Y.). Plasmid DNA was isolated from *S. thermophilus* as described by Anderson and McKay (*Appl. Environ. Microbiol.* 46:549–552 (1983)). Bacteriophage genomic DNA was isolated using the Qiagen Lambda Kit (Valencia, Calif.) according the manufacturer's instructions. When required, DNA was extracted from agarose gels using the QIAquick Gel Extraction Kit (Qiagen).

Polymerase Chain Reaction (PCR), DNA Sequencing and Sequence Analysis. PCR reactions were performed in a Hybaid PCR Express thermal cycler (Middlesex, United Kingdom) using DNA primers synthesized by Integrated DNA Technologies, Inc. (Coralville, Iowa). The primers used are listed in Table 2. Cycle sequencing reactions and DNA sequence determination were performed by the University of California Davis Sequencing Center (Davis, Calif.). DNA sequences were analyzed using the DNAsis sequence analysis package v2.5 (Hitachi Software Engineering Co., Ltd., Yokohama, Japan). Protein and nucleic acid homology searches were performed using the BLAST network services at the National Center for Biotechnology Information (Bethesda, Md.) web site.

Bacterial Transformation. Electroporation of *E. coli* stain MC1061 was conducted as described by Dower et al (Nucleic Acids Res. 16:6127–6145 (1988)). Electroporation of *S. thermophilus* was accomplished utilizing a method based on the Holo-Nes protocol (Sturino and Steele, *Journal of Dairy Science.* In Review (2000)). All electroporations were performed using a Bio Rad Gene Pul ser (Bio-Rad Laboratories, Richmond, Calif.) apparatus configured to 25 μF, 2.5 kV and 200 Ω.

Bacteriophage Propagation and Characterization. Bacteriophages used are listed in Table 1. *S. thermophilus* bacteriophages were propagated and enumerated as described by Jarvis (*Appl. Environ. Microbiol.* 47:1031–1038 (1984) except that *S. thermophilus* hosts were grown at 42° C. in Elliker-B broth. Efficiency of plaquing (EOP) analysis was performed as described elsewhere (Sturino and Steele, *Journal of Dairy Science.* In Review (2000)). Bacteriophages were classified as pac- or cos-type phages according to the PCR based method described by Le Marrec et. al. (*Appl. Environ. Microbiol.* 63:3246–3253 (1997)).

Construction of a Basal Antisense RNA Expression Vector. Of the vector systems tested to date, only those that replicate via a rolling circle (RC) mechanism are transformable into strains of *S. thermophilus* (data not shown). As a result, the antisense RNA expression systems described here are based on the high-copy number, RC plasmid pNZ123 (De Vos, *FEMS Microbiol. Rev.* 46:281–295 (1987)). The plasmid pTRK593 (Walker and Klaenhammer, *Appl. Environ. Microbiol.* 66:310–319 (2000)) was digested with Bg/II and the 0.6-kb fragment containing the strong Lb. *acidophilus* ATCC4356 P6 promoter (P$_6$) (Djordjevic, et al., *Can. J. Microbiol.* 43:61–69 (1997)), a multiple cloning site and downstream coliphage T7 transcriptional terminator (T$_{T7}$), was ligated into the Sau3AI site of the RC vector pNZ123. FIG. 1 shows a map of the resulting 3.0-kb plasmid, designated pNZ123::P$_6$.

Classification of *S. thermophilus* Bacteriophages. Six *S. thermophilus* bacteriophages that differ in genomic restriction pattern (data not shown) were classified into either of two groups (cos-type or pac-type) based on the diagnostic PCR method described by Le Marrec (*Appl. Environ. Microbiol.* 63:3246–3253 (1997)). PCR analysis indicated that four bacteriophages, designated κ3, κ4, κ9, and κ10, were cos-type bacteriophages, while two bacteriophages, designated κ6 and κ12, were pac-type bacteriophages (data not shown).

EXAMPLE 2

Antisense Helicase

Helicase-Based Antisense RNA Expression System. Sequence data from the complete genomic sequence of *S.*

TABLE 2

| Designation | Primer Sequence[a] |
|---|---|
| JMSp1[a] | 5'-AAA <u>CTG CAG</u> GCT TGC AAG ATT GAA GAC C-3' (SEQ ID NO: 3) |
| JMSp2[a] | 5'-AAA <u>CTG CAG</u> CCG TCT TT GAT AGA TCCG-3' (SEQ ID NO: 4) |
| JMSp3 | 5'-GGA GCG TGA TTT TTA TGG-3' (SEQ ID NO: 5) |
| JMSp4[a] | 5'-AAA <u>CTG CAG</u> CAA CAC CCA AGA GCC-3' (SEQ ID NO: 6) |
| JMSp5[a] | 5'-AAA <u>CTG CAG</u> GTT GCA ATA ACC TGC GG-3' (SEQ ID NO: 7) |
| JMSp6[b] | 5'-<u>GGA ATT CCA</u> CTT GTC AGA TGT CGT TTC C-3' (SEQ ID NO: 8) |
| JMSP7[b] | 5'-<u>GGA ATT CCC</u> CAT AAT CTT CGT CGG TCC-3' (SEQ ID NO: 9) |

[a]Primer encoded PstI sites are underlined.
[b]Primer encoded EcoRI sites are underlined.

Figure 2:
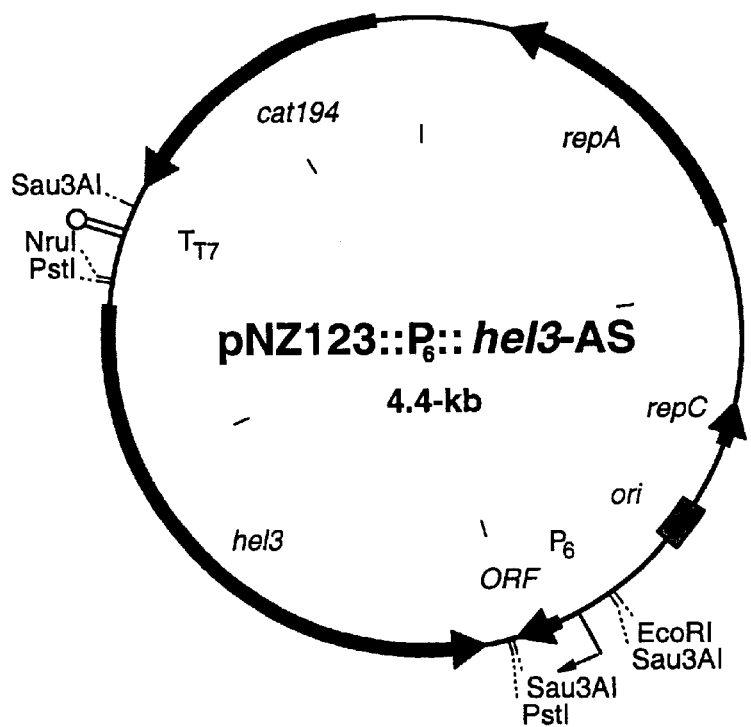
FIG. 2 depicts bacteriophage κ3-derived antisense (AS)- and sense (S)-hel3 (helicase gene isolated from cos-type κ3 bacteriophage) expression vectors pNZ123::$P_6$::hel3-AS pNZ123::$P_6$::hel3-S, respectively. A 1.4-kb fragment containing the complete κ3-derived hel3 allele was amplified by PCR using PsiI-tagged primers JMSp1 (5'-AAA CTG CAGGCT TGC AAG ATT GAA GAC C-3', SEQ ID NO: 3) and JMSp2 (5'-AAACTG CAGCCG TCT TTG ATA GAT CCG-3', SEQ ID NO: 4). The resulting fragment was subsequently cloned into the unique PstI site present on the basal RNA expression vector pNZ123::$P_6$. The direction of transcription from the $P_6$ promoter is marked by an arrow.
Figure 2:
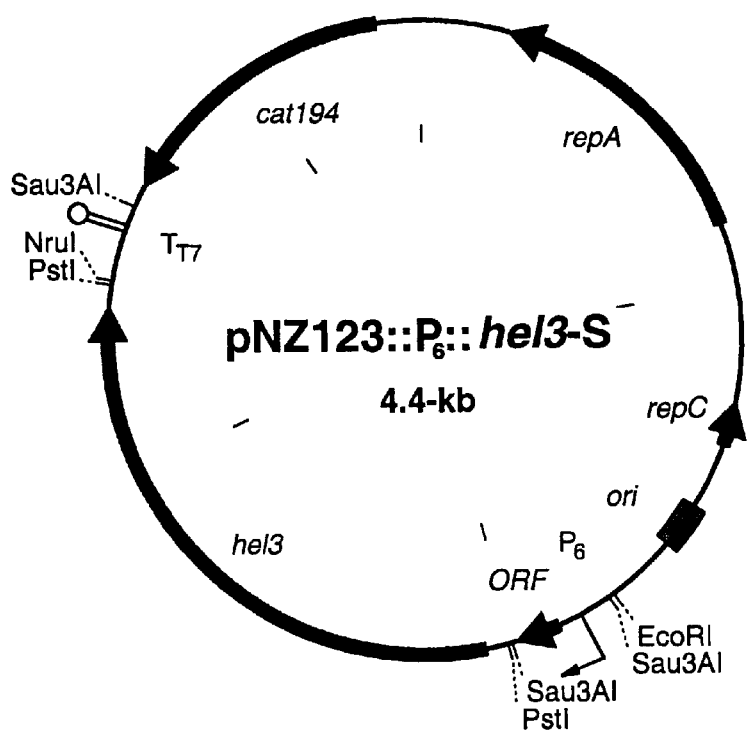

*thermophilus* bacteriophage DT1 (Tremblay and Moineau, *Virology*. 255:63–76 (1999)) was used to design PstI-tagged primers located 5' (JMSp1; 5'-AAA CTG CAGGCT TGC AAG ATT GAA GAC C-3', SEQ ID NO: 3) and 3' (JMSp2; 5'-AAA CTG CAGCCG TCT TT GAT AGA TCCG-3', SEQ ID NO: 4) of the DT1 putative D gene (SEQ ID NO: 1). Using cos-type bacteriophage κ3 genomic DNA as a template during PCR, primers JMSp1 and JMSp2 were used to amplify a 1.4-kb fragment that contained the κ3 helicase allele, designated hel3. The resultant 1.4-kb, hel3-containing fragment was gel purified, digested with PstI and cloned between the P6 promoter and the T7 transcriptional terminator, in either orientation (i.e. sense vs. antisense) relative to the direction of transcription from the $P_6$ promoter, into the PstI site of pNZ123::$P_6$. Insert orientation was confirmed by differential PCR amplification using the pNZ123::$P_6$-derived, $P_6$-specific primer JMSp3 (5'-GGA GCG TGA TTT TTA TGG-3', SEQ ID NO: 5) and either JMSp1 or JMSp2 (data not shown). The resultant constructs, designated pNZ123::$P_6$::hel3-AS (i.e. hel3 cloned in the antisense orientation relative to the $P_6$ promoter; FIG. 2) and pNZ123::$P_6$::hel3-S (i.e. hel3 cloned in the sense orientation relative to the $P_6$ promoter; FIG. 2), were subsequently electroporated into *S. thermophilus* MTC130 for physiological assessment. The plasmid pNZ123::$P_6$::hel3-S was included in this study as a negative control to exclude the possibility that any observed drop in EOP or plaque size might be attributed to the increased metabolic burden associated with RNA expression from these high copy number vectors and not antisense RNA-specific effects per-say.

The parental strain *S. thermophilus* MTC130, vector control strains MTC130 (pNZ123), MTC130 (pNZ123::$P_6$), and MTC130 (pNZ123::$P_6$::hel3-S), and the antisense hel3 expression strain MTC130 (pNZ123::$P_6$::hel3-AS) were challenged with individual cos-type (i.e. phages κ3, κ4, κ9, and κ10) or pac-type phages (i.e. κ6 and κ12) during standard plaque assays. The tabulated results of listed in Table 3 and Table 4, respectively.

parental strain (Table 3). The expression of antisense hel3 (derived from a cos-type phage) had no effect on pac-type phage EOP or mean plaque diameter (Table 4). Phages propagated on vector control strains generally gave rise to smaller plaques (usually a 20% reduction in mean plaque diameter) when compared to the MTC130 parental strain but did not exhibit significant reductions in EOP. Interestingly, cos-type phages appeared to be particularly sensitive to propagation on these vector control stains. The mechanism for this reduction is yet unknown.

EXAMPLE 3

Antisense Primase

Primase-Based Antisense RNA Expression System. Sequence data from the complete genomic sequence of *S. thermophilus* bacteriophage DT1 was again used to design PstI-tagged primers. On this occasion, the primers were located 5' (JMSp4; 5'-AAA CTG CAGCAA CAC CCA AGA GCC-3', SEQ ID NO: 6) and 3' (JMSp5; 5'-AAA CTG CAGGTT GCA ATA ACC TGC GG-3', SEQ ID NO: 7) of the DT1 putative primase allele (SEQ ID NO: 2). The cos-type bacteriophage κ3 genomic DNA was used as a template during PCR, and primers JMSp4 and JMSp5 were used to amplify a 1.4-kb fragment that contained a truncated allele of the κ3 primase gene, designated pri3ΔRBS. The truncated pri3ΔRBS allele was devoid of its putative RBS and the first 26-bp of the coding region.

Figure 3:
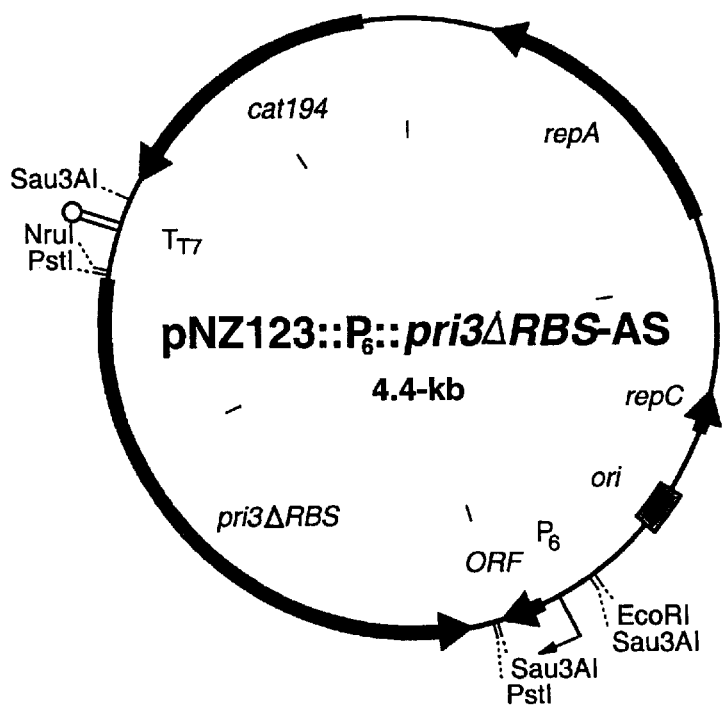
FIG. 3 depicts bacteriophage κ3-derived antisense (AS)- and sense (S)-pri3ΔRBS (primase gene isolated from cos-type κ3 bacteriophage lacking ribosome binding site) expression vectors pNZ123::$P_6$::pri3ΔRBS-AS and pNZ123::$P_6$::pri3ΔRBS-S, respectively. A 1.4-kb fragment containing a truncated allele, designated pri3ΔRBS, of the κ3 primase gene was amplified by PCR using PstI-tagged primers JMSp4 (5'-AAA CTG CAGCAA CAC CCA AGA GCC-3', SEQ ID NO: 6) and JMSp5 (5'-AAA CTG CAGGTT GCA ATA ACC TGC GG-3', SEQ ID NO: 7). The resulting fragment was subsequently cloned into the unique PstI site present on the basal RNA expression vector pNZ123::P$_6$. The direction of transcription from the P$_6$ promoter is marked by an arrow.
Figure 3:
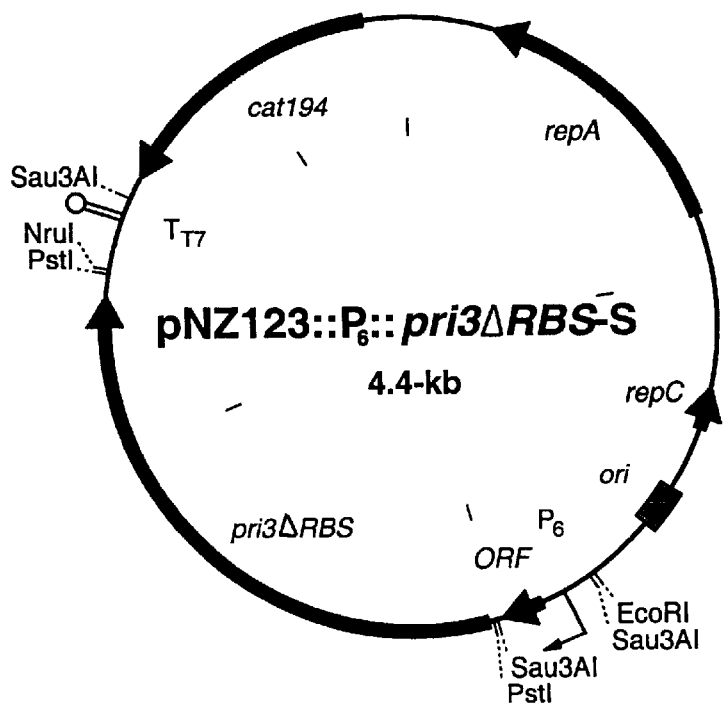

Again, the resultant 1.4-kb, pri3ΔRBS-containing fragment was gel purified, digested with PstI and cloned between the P6 promoter and the T7 transcriptional terminator, in either orientation (i.e. sense vs. antisense) relative to the direction of transcription from the $P_6$ promoter, into the PstI site of pNZ123::$P_6$. Insert orientation was confirmed by differential PCR amplification using the primers JMSp3 and either JMSp4 or JMSp5 (data not shown). The new constructs, designated pNZ123::$P_6$::pri3ΔRBS-AS (FIG. 3) and

TABLE 3

| Plasmid Used in Host Strain MTC 130 | Phage κ3 | | Phage κ4 | | Phage κ9 | | Phage κ10 | |
| --- | --- | --- | --- | --- | --- | --- | --- | --- |
| | EOP | Diameter | EOP | Diameter | EOP | Diameter | EOP | Diameter |
| Control | 1.0 | 2.7 mm | 1.0 | 2.9 mm | 1.0 | 2.6 mm | 1.0 | 2.4 mm |
| pNZ123 | 1.0 | 2.3 mm | 1.1 | 2.2 mm | 1.0 | 2.3 mm | 0.9 | 2.0 mm |
| pNZ123::$P_6$ | 0.9 | 2.3 mm | 1.1 | 2.1 mm | 0.9 | 2.4 mm | 0.9 | 1.9 mm |
| pNZ123::$P_6$::hel3-S | 0.9 | 2.2 mm | 1.2 | 2.3 mm | 1.0 | 2.0 mm | 1.1 | 1.8 mm |
| pNZ123::$P_6$::hel3-AS | 0.6 | 0.6 mm | 0.8 | 0.7 mm | 0.5 | 0.6 mm | 0.4 | 0.6 mm |

TABLE 4

| Plasmid Used in Host Strain MTC130 | Phage κ6 | | Phage κ12 | |
| --- | --- | --- | --- | --- |
| | EOP | Diameter | EOP | Diameter |
| (control) | 1.0 | 1.8 mm | 1.0 | 2.2 mm |
| (pNZ123) | 0.8 | 1.7 mm | 0.8 | 2.0 mm |
| (pNZ123::$P_6$) | 0.8 | 1.8 mm | 0.7 | 2.0 mm |
| (pNZ123::$P_6$::hel3-S) | 0.9 | 1.7 mm | 1.0 | 2.0 mm |
| (pNZ123::$P_6$::hel3-AS) | 0.8 | 1.8 mm | 0.9 | 2.0 mm |

The expression of antisense hel3 by strain MTC130 (pNZ123::$P_6$::hel3-AS) had a marginal, but consistent, impact on cos-type bacteriophage replication and caused a 20 to 60% reduction in EOP with a concomitant 70–80% decrease in mean plaque diameter relative to the MTC130 pNZ123::$P_6$::pri3ΔRBS-S (FIG. 3) were electroporated into *S. thermophilus* MTC130 for physiological assessment.

The parental strain *S. thermophilus* MTC130, vector control strains MTC130 (pNZ123::$P_6$) and MTC130 (pNZ123::$P_6$::pri3ΔRBS-S), and the antisense pri3ΔRBS expression strain MTC130 (pNZ123::$P_6$::pri3ΔRBS-AS), were challenged with individual cos- (i.e. phages κ3, κ4, κ9, and κ10) or pac-type phages (i.e. κ6 and κ12) during standard plaque assays. The tabulated results of these studies are found in Table 5 and Table 6, respectively.

TABLE 5

| Plasmid Used in Host Strain MTC 130 | Phage κ3 | | Phage κ4 | | Phage κ9 | | Phage κ10 | |
| --- | --- | --- | --- | --- | --- | --- | --- | --- |
| | EOP | Diameter | EOP | Diameter | EOP | Diameter | EOP | Diameter |
| Control | 1.0 | 2.7 mm | 1.0 | 2.9 mm | 1.0 | 2.6 mm | 1.0 | 2.4 mm |
| pNZ123::P$_6$ | 0.9 | 2.3 mm | 1.1 | 2.2 mm | 1.0 | 2.3 mm | 0.9 | 2.0 mm |
| pNZ123::P$_6$::pri3ΔRBS-S | 1.0 | 2.3 mm | 1.0 | 2.1 mm | 0.9 | 2.4 mm | 0.9 | 1.9 mm |
| pNZ123::P$_6$::pri3ΔRBS-AS | $1.9 \times 10^{-6}$ | pinpoint | $2.3 \times 10^{-6}$ | pinpoint | $1.8 \times 10^{-6}$ | pinpoint | $<1.2 \times 10^{-8}$ | NA |

NA = Not Applicable

TABLE 6

| Plasmid Used in Host Strain MTC130 | Phage κ6 | | Phage κ12 | |
| --- | --- | --- | --- | --- |
| | EOP | Diameter | EOP | Diameter |
| Control | 1.0 | 1.8 mm | 1.0 | 2.2 mm |
| pNZ123::P$_6$ | 1.2 | 1.6 mm | 0.9 | 1.9 mm |
| pNZ123::P$_6$::pri3ΔRBS-S | 1.1 | 1.8 mm | 0.9 | 2.0 mm |
| pNZ123::P$_6$::pri3ΔRBS-AS | 0.9 | 1.8 mm | 1.0 | 2.0 mm |

The expression of antisense pri3ΔRBS by strain MTC130 pNZ123::P$_6$::pri3ΔRBS-AS) was found to have a significant impact on cos-type bacteriophage replication (i.e. κ3, κ4, κ9, and κ10) and reduced EOPs to $1.9 \times 10^{-6}$ to $<1.2 \times 10^{-8}$ (relative to the MTC130 parental strain) and gave rise to pinpoint plaques (i.e. less than 0.5 mm in diameter; Table 5). As was seen with hel3, the expression of antisense pri3ΔRBS (derived from a cos-type phage) had no effect on pac-type phage (κ6 and κ12) EOP or mean plaque diameter (Table 6).

EXAMPLE 4

Antisense Helicase—Exponentially Replicating Vector

Phage-encoded resistance (PER) has previously been demonstrated to be an effective means of inhibiting *S. thermophilus* bacteriophage replication (Stanley et al., *FEMS Micro. Letters* 182:271–277 (2000)). By providing a bacteriophage origin of DNA replication (ori) in trans on a recombinant plasmid, PER vectors are able to act as molecular decoys and titer away factors that are required for efficient replication of the invading bacteriophage's genome. In *Lactococcus lactis*, Walker and Klaenhammer reported that the combination of a bacteriophage origin with a antisense expression cassette on a single plasmid (i.e. in cis) was able to increase the level of bacteriophage resistance beyond the level of either resistance mechanism alone (*Appl. Environ. Microbiol.* 66:310–319 (2000)). In this case, the plasmid-linked bacteriophage origin acts as an alternative origin of plasmid replication that, once triggered following bacteriophage infection, delivers exponential amplification of the vector, thereby increasing the dose of antisense RNA.

Figure 4:
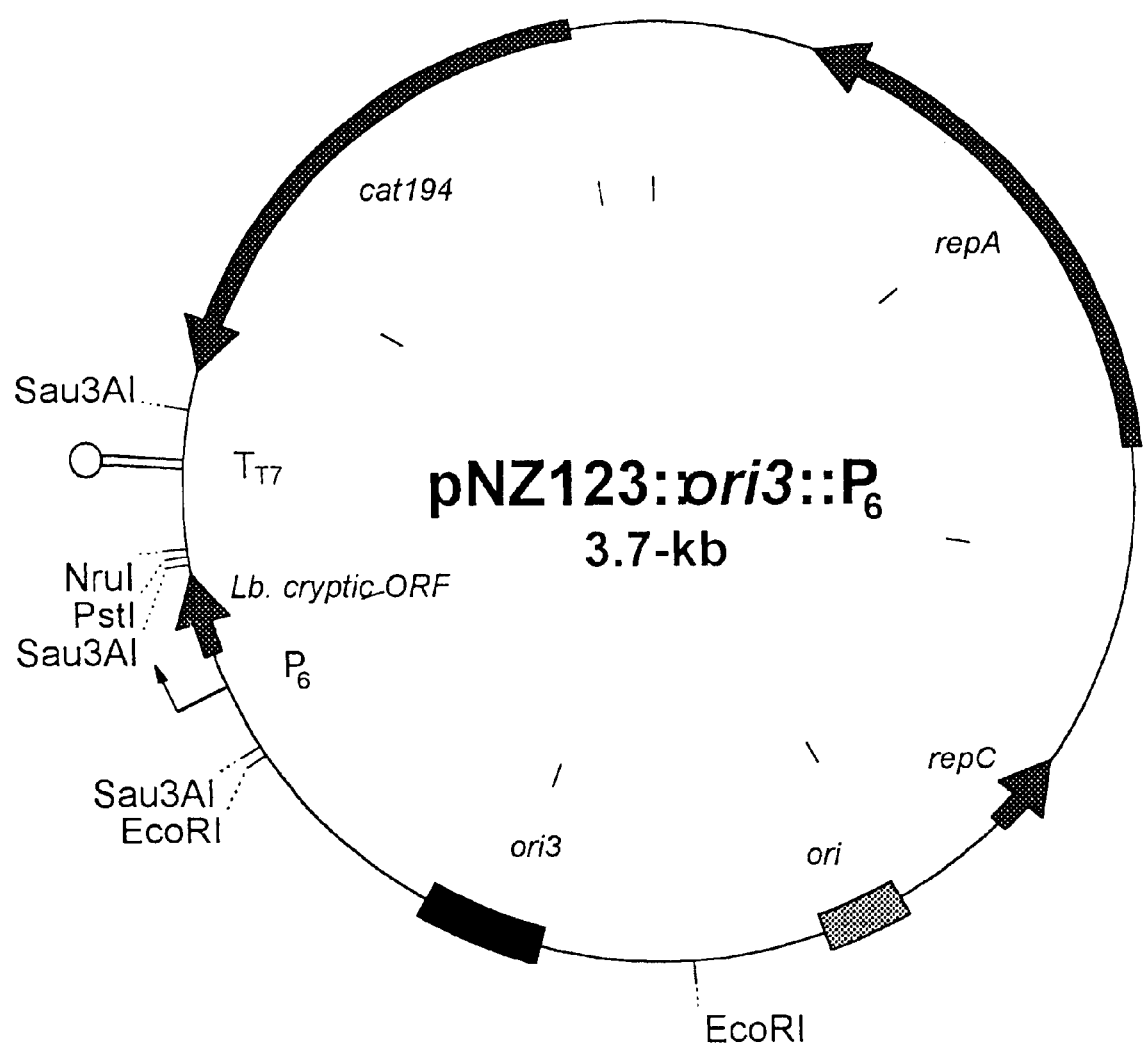
FIG. 4 depicts the high-copy number exponentially-replicating RNA expression vector pNZ123::ori3::P$_6$ (ori3 origin of replication isolated from cos-type κ3 bacteriophage).

Construction of the Base Exponentially-Replicating Antisense RNA Expression Vector. Sequence data from the complete genomic sequence of *S. thermophilus* bacteriophage DT1 was used to design EcoRI-tagged primers located 5' (JMSp6; 5'-G<u>GAATTC</u>CA CTT GTC AGA TGT CGT TTC C-3', SEQ ID NO: 8) and 3' (JMSp7; 5'-G <u>GA ATT C</u>CC CAT AAT CTT CGT CGG TCC-3', SEQ ID NO: 9) of the DT1 putative origin of DNA replication. Using cos-type bacteriophage κ3 genomic DNA as a template during PCR, primers JMSp6 and JMSp7 were used to amplify a 0.7-kb fragment that contained the κ3 origin of DNA replication, designated ori3. The resultant 0.7-kb, ori3-containing fragment was gel purified, digested with EcoRI and ligated into the unique EcoRI site of pNZ123::P$_6$, which is located upstream of the P$_6$ promoter (i.e. 5' relative to the direction of transcription). A map of the resultant 3.7-kb plasmid, designated pNZ123::ori3::P$_6$, is shown in FIG. 4.

Figure 5:
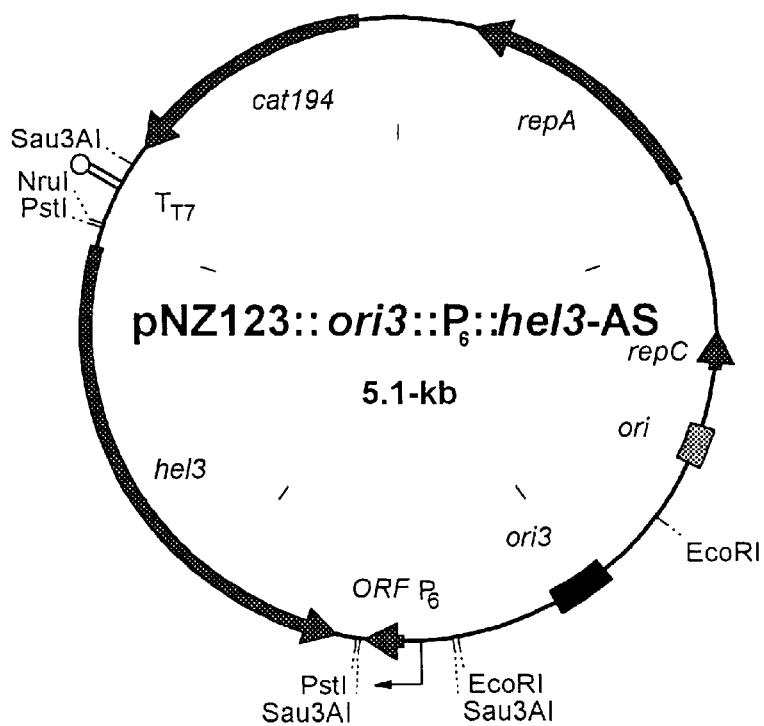
FIG. 5 depicts the exponentially-replicating bacteriophage κ3-derived antisense (AS)-hel3 and sense (S)-hel3 RNA expression vectors pNZ123::ori3::P$_6$::hel3-AS and pNZ123 ::ori3::P$_6$::hel3-S, respectively.
Figure 5:
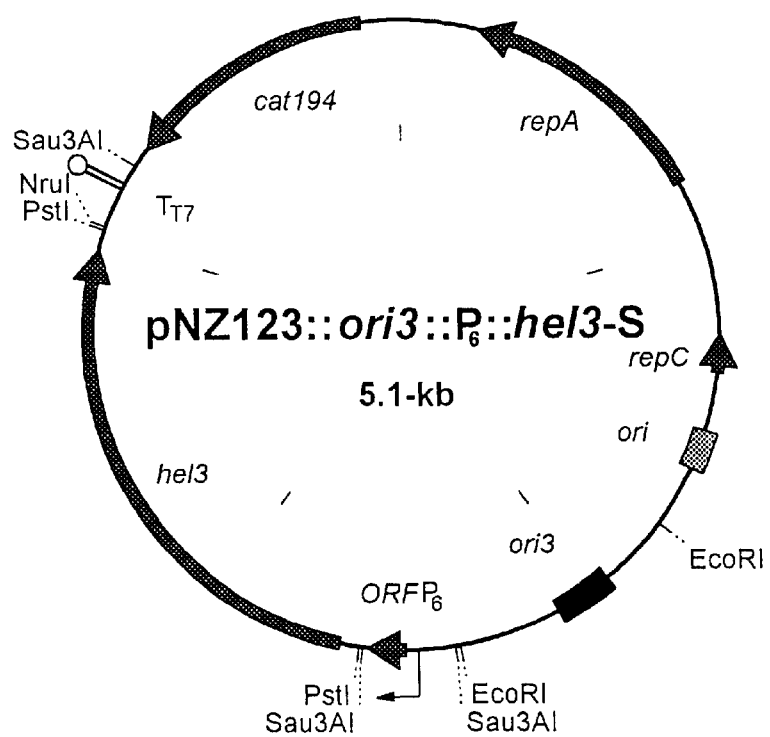

Exponentially-replicating, helicase-based antisense RNA expression system. Using cos-type bacteriophage κ3 genomic DNA as a template during PCR, primers JMSp1 and JMSp2 were again used to amplify a 1.4-kb fragment that contained the κ3 helicase allele, designated hel3. The resultant 1.4-kb, hel3-containing fragment was gel-purified, digested with PstI and cloned between the P6 promoter and the T7 transcriptional terminator, in either orientation (i.e. sense vs. antisense) relative to the direction of transcription from the P$_6$ promoter, into the unique PstI site of pNZ123::ori3::P$_6$. Insert orientation was confirmed by differential PCR amplification using the pNZ123::P$_6$-derived, P$_6$-specific primer JMSp3 and either JMSp1 or JMSp2 (data not shown). The construct designated pNZ123::ori3::P$_6$::hel3-AS (i.e. hel3 cloned in the antisense orientation relative to the P$_6$ promoter; FIG. 5 was successfully confirmed and was subsequently electroporated into *S. thermophilus* MTC130 for physiological assessment. The control plasmid pNZ123::ori3::P$_6$::hel3-S (i.e. hel3 cloned in the sense orientation relative to the P$_6$ promoter; FIG. 5 was not available.

The parental strain *S. thermophilus* MTC130, vector control strains MTC130 (pNZ123::P$_6$) and MTC130 (pNZ123::ori3::P$_6$), and the antisense hel3 expression strain MTC130 (pNZ123::ori3::P$_6$::hel3-AS), were challenged with cos-type bacteriophage κ3 during standard plaque assays. The tabulated results of these studies are listed in Table 7.

TABLE 7

| Plasmid Used in Host Strain | Phage κ3 | |
| --- | --- | --- |
| MTC 130 | EOP | Diameter |
| Control | 1.0 | 2.4 mm |
| pNZ123::P$_6$ | 0.8 | 2.1 mm |
| pNZ123::P$_6$::hel3-AS | 0.6 | 0.6 mm |
| pNZ123::ori3::P$_6$ | $8.8 \times 10^{-7}$ | pinpoint |
| pNZ123::ori3::P$_6$::hel3-AS | $<3.3 \times 10^{-9}$ | NA |

NA = Not Applicable

As previously described in other systems (Walker and Klaenhammer, *Appl. Environ. Microbiol.* 66:310–319 (2000); Stanley et al., *FEMS Micro. Letters* 182:271–277 (2000)), the presence of a bacteriophage origin of DNA replication (ori3) alone on the control plasmid pNZ123::ori3::P$_6$ had a significant impact on κ3 replication. The presence of plasmid-linked ori3 in control strain MTC130 (pNZ123::ori3::$P_6$) was found to reduce EOP's to $8.8 \times 10^{-7}$ (relative to the MTC130 parental strain) and gave rise to pinpoint plaques (i.e. less than 0.5 mm in diameter; Table 7). The exponential delivery of antisense hel3 RNA by strain MTC130 (pNZ123::ori3::$P_6$::hel3-AS), however, was found to completely abolish bacteriophage κ3 replication and reduced EOP's below the assay's limit of detection (i.e. $<3.3 \times 10^{-9}$). To date, no recombinant or mutant ori3 resistant/antisense hel3 resistant derivatives of bacteriophage κ3 have been isolated when propagated on MTC130 (pNZ123::ori3::$P_6$::hel3-AS).

The foregoing examples are illustrative of the present invention, and are not to be construed as limiting thereof. The invention is described by the following claims, with equivalents of the claims to be included therein.

That which is claimed is:

1. An isolated nucleic acid encoding an antisense oligonucleotide that binds to an RNA sequence encoded by a *Streptococcus thermophilus* bacteriophage, which antisense oligonucleotide inhibits the replication of said bacteriophage in a *Streptococcus thermophilus* cell;
   wherein said RNA is a phage protein mRNA, said phage protein selected from the group consisting of primase and helicase;
   and wherein said phage is selected from the group consisting of cos-type phages and pac-type phages.

2. The isolated nucleic acid according to claim 1, which nucleic acid is at least 8 nucleotides in length.

3. The isolated nucleic acid according to claim 1, wherein said phage is a cos-type phage.

4. The isolated nucleic acid according to claim 1, wherein said phage is a pac-type phage.

5. The isolated nucleic acid according to claim 1 having a sequence in antisense orientation to at least an 8 nucleotide portion of the sequence given herein as SEQ ID NO: 1.

6. The isolated nucleic acid according to claim 1 having a sequence in antisense orientation to at least an 8 nucleotide portion of the sequence given herein as SEQ ID NO: 2.

7. A recombinant nucleic acid comprising a nucleic acid encoding an antisense oligonucleotide operatively associated with a promoter, wherein said antisense oligonucleotide binds to an RNA sequence encoded by a *Streptococcus thermophilus* bacteriophage, which antisense oligonucleotide inhibits the replication of said bacteriophage in a *Streptococcus thermophilus* cell;
   wherein said RNA is a phage protein mRNA, said phage protein selected from the group consisting of primase and helicase;
   and wherein said phage is selected from the group consisting of cos-type phages and pac-type phages.

8. A recombinant nucleic acid according to claim 7, wherein said nucleic acid encoding an antisense oligonucleotide is at least 8 nucleotides in length.

9. The recombinant nucleic acid according to claim 7, wherein said nucleic acid is a plasmid.

10. The recombinant nucleic acid according to claim 7, wherein said nucleic acid comprises DNA.

11. The recombinant nucleic acid according to claim 7, wherein said promoter is constitutively active in a *Streptococcus thermophilus* cell.

12. The recombinant nucleic acid according to claim 7, wherein said recombinant nucleic acid further comprises a phage origin of replication.

13. The recombinant nucleic acid according to claim 7, wherein said phage is a cos-type phage.

14. The isolated nucleic acid according to claim 7, wherein said phage is a pac-type phage.

15. The recombinant nucleic acid according to claim 7 having a sequence in antisense orientation to at least an 8 nucleotide portion of the sequence given herein as SEQ ID NO: 1.

16. The recombinant nucleic acid according to claim 7 having a sequence in antisense orientation to at least an 8 nucleotide portion of the sequence given herein as SEQ ID NO: 2.

17. A *Streptococcus thermophilus* cell containing a recombinant nucleic acid, said recombinant nucleic acid comprising a nucleic acid encoding an antisense oligonucleotide operatively associated with a promoter, wherein said antisense oligonucleotide binds to an RNA sequence encoded by a *Streptococcus thermophilus* bacteriophage, which antisense oligonucleotide inhibits the replication of said bacteriophage in a *Streptococcus thermophilus* cell;

wherein said RNA is a phage protein mRNA, said phage protein selected from the group consisting of primase and helicase;

and wherein said phage is selected from the group consisting of cos-type phages and pac-type phages.

18. A cell according to claim 17, wherein said nucleic acid encoding an antisense oligonucleotide is at least 8 nucleotides in length.

19. A starter culture comprising *Streptococcus thermophilus* cells according to claim 17.

20. A method of fermenting milk to produce a fermentation product, comprising the steps of:

(a) combining milk with *Streptococcus thermophilus* cells according to claim 17 to produce a fermentation media; and then (b) fermenting said milk with said *Streptococcus thermophilus* cells to produce said fermentation product.

* * * * *